United States Patent [19]

Mishelevich et al.

[11] Patent Number: 5,363,842
[45] Date of Patent: Nov. 15, 1994

[54] INTELLIGENT INHALER PROVIDING FEEDBACK TO BOTH PATIENT AND MEDICAL PROFESSIONAL

[75] Inventors: David J. Mishelevich, Cupertino; Ted W. Lanpher, Atherton; Gregory B. Lanpher, York; James Long, Sunnyvale, all of Calif.

[73] Assignee: Circadian, Inc., San Jose, Calif.

[21] Appl. No.: 811,398

[22] Filed: Dec. 20, 1991

[51] Int. Cl.$^5$ .............................. A61M 11/00
[52] U.S. Cl. .................... 128/200.14; 128/200.23; 128/204.23; 128/205.23
[58] Field of Search ............ 128/200.14, 200.23, 128/203.12, 204.21, 204.23, 725, 205.23

[56] References Cited

U.S. PATENT DOCUMENTS

| | | | |
|---|---|---|---|
| 3,991,304 | 11/1976 | Hillsman | 128/725 |
| 4,942,544 | 7/1990 | McIntosh et al. | 364/413.02 |
| 4,984,158 | 1/1991 | Hillsman | 128/725 |
| 5,152,456 | 10/1992 | Ross et al. | 128/200.16 |

OTHER PUBLICATIONS

"Deposition of Pressurized Aerosols In the Human Respiratory Tract" by Newman et al., Thorax, 1981, 36, 52–55.
"How Should a Pressurized β-Adrenergic Bronchodilator be Inhaled?" by Newman et al., Eur. J. Respir Dis (1981) 62, 3–21.

Primary Examiner—Edgar S. Burr
Assistant Examiner—Aaron J. Lewis
Attorney, Agent, or Firm—Wilson, Sonsini, Goodrich & Rosati

[57] ABSTRACT

The present invention detects how much air is inhaled through the inhaler with what time course (including such derived measurements as how much volume is inspired within the bounds of a given flow range) as well as certain events such as the triggering of the release of aerosol. The system can be set up to compare the resultant time course to either (a) a standard target envelope (e.g., one or more of flow, volume, and time) for that patient programmed into the intelligent inhalation device by a healthcare professional. Based on the comparison, the success or failure of effective inhaler actuation and aerosol inspiration can be signaled to the patient (e.g., visually or through sound) and may be recorded with a time and date stamp for later decoding and evaluation of the invention, the device would also possess the ability to signal the patient to continue post-inspiratory breath holding for use in interpreting the success of medication delivery.

33 Claims, 12 Drawing Sheets

LED DISPLAY and BEEPER DRIVER

OVERVIEW of PROTOCOL for CLOSING the THERAPEUTIC LOOP

PROCESS for UTILIZATION by the PATIENT

INTELLIGENT INHALER PROVIDING FEEDBACK TO BOTH PATIENT AND MEDICAL PROFESSIONAL

BACKGROUND OF THE INVENTION

1. Field of Invention

The field of the present invention relates generally to an inhaler device for aerosol delivery of medicine. More particularly, the present invention is directed to a device for improving medication compliance by providing feedback regarding correct and consistent usage of medicine inhalers to a patient and/or professional such as a physician, pharmacist, or therapist. The present invention is further directed to a method by which such professionals can track the usage of medicine inhalers between visits, and modify medicinal therapy based on downloading of this information to a clinical workstation allowing display and analysis.

2. The Prior Art

Getting patients to correctly use medicine inhalers is a major problem. Estimates indicate as few as one quarter of patients using inhalers do so correctly [Orehek, J., "Patient Error in Use of Bronchodilator Metered Aerosols," *British Medical Journal*, 1:76 (1976); Paterson, I. C. and G. K. Crompton, "Use of Pressurized Aerosols by Asthmatic Patients," *British Medical Journal*, 1:76-77 (1976); Saunders, K. B., "Misuse of Inhaled Bronchodilator Agents," *British Medical Journal*, 1:1037-1038 (1965); Shim, C., and M. H. Williams, "The Adequacy of Inhalation of Aerosol from Canister Nebulizers," *The American Journal of Medicine*, 69:891-894 (1980)]. In addition to unnecessary patient morbidity and mortality, an unfortunate consequence is that patients may stop taking their medications because they are not seeing any or enough benefit. Conversely, having failed to obtain expected benefits through prescribed usage, some patients will overuse medications and thereby increase the risk of side effects caused by higher than normal dosages (e.g., fungal infections in the mouth and throat or nervous system effects caused by medication absorbed in the gastro-intestinal tract).

These problems are especially evident in the case of aerosol pharmaceuticals delivered by hand-held inhalers. Hand-held metered dose inhalers (MDIs) are a preferred method of treatment for common respiratory ailments, since the delivery of medication directly to its intended site of action in the lungs allows a reduction in dosage by an order of magnitude or greater. However, certain of these compounds, such as anti-inflammatory corticosteroids, may take many weeks of administration before having a significant effect. Moreover, the inhalation and breath-holding maneuver required for successful delivery of aerosol to the lower airways is counterintuitive and poorly understood by most patients. Thus, a patient may be compliant in using the medication when prescribed, but unsuccessful in using it in the correct manner.

When therapeutic results are not obtained, it may not be evident to the physician which step(s) in the process are the problem. Relevent questions, for example, are "was the medication not taken at all?", "was it taken at the correct intervals and in proper relationship to exposure to allergens or other irritants?", and "was the inhalation performed correctly?".

Another problem the physician faces is how to interpret variability in therapeutic response. Is the variability due to some fundamental change in the patient's condition (e.g., the patient now has a low-grade upper respiratory infection) or is it caused by differences in delivered medication dosage?

Deposition of aerosol medication in the human lung is primarily determined by two processes, inertial impaction and gravitational sedimentation. Impaction of aerosols in the lungs occurs primarily at airway bifurcations, and has been shown in scintigraphic studies to increase as a function of flow rate. Sedimentation involves gravitational settling of aerosol particles on the airways and alveoli. Newman, S. P., Pavia, D., Garland, N. and S. W. Clarke, "Effects of Various Inhalation Modes on the Deposition of Radioactive Pressurized Aerosols," *European J. Respiratory Dis.*, Supplement 119, 63:57-65, (1982) demonstrated that the percentage of aerosol deposited in the lungs of patients was significantly greater when the patients held their breath for ten seconds than when breath holding was only four seconds.

Thus, for aerosol to be deposited in the lower airways, the primary site of action for common medications such as corticosteroids and bronchodilators, the patient must coordinate the release of medication, inhale slowly enough to minimize loss of medicine through impaction in the throat and upper airways, and breath hold long enough to allow time for small particles to settle. In practice, this means an inhalation rate below one liter per second, and a breath hold for up to ten seconds.

A hand-held (e.g., metered or unit-dose) inhaler currently is a passive device that provides no information regarding the medication actually delivered. Orehek et al. found that only five of twenty asthmatic patients correctly inhaled. "The other 15 patients failed either to inspire deeply or hold their breath afterwards, or both, or poorly coordinated the puff and the inspiration." Orehek et al., "Patient Error in Use of Bronchodilator Metered Aerosols," *British Medical Journal*, 1:76, (1976).

For example, it has been found that in a group of 30 acute asthmatic patients directly observed in a clinical setting, 47% (14 patients) used incorrect technique. The fourteen patients with inadequate technique were then trained. Ten of them were retested after an interval of one day to one month. Five of the patients were still using their inhalers correctly; the other five had reverted to their original incorrect techniques. Shim, C., and M. H. Williams, "The Adequacy of Inhalation of Aerosol from Canister Nebulizers," *The American Journal of Medicine*, 69:891-894 (1980).

The device and approach described herein would have provided immediate feedback to the patients that they had reverted to incorrect use of their inhalers, and provided them with specific guidance as to what corrective action was required. Thus, retraining would not have had to wait until their next visit to the clinic.

The present approach also fosters the delivery of a uniform dose to the target sites of the patient's lungs upon each inhaler usage with the expectation of consistent therapeutic response. Thus, if the patient's symptoms or condition changes, the physician can evaluate the change with reasonable assurance that the difference is not simply due to a variation in medication dosage. By making data regarding the patient's inhaler use during the entire period between clinic visits available to the physician, therapy can be managed on a more informed basis.

It has been observed that, "The lung presents a significant barrier to the penetration of drug particles of a size small enough to maximize therapeutic efficacy." Padfield, J. M., "Principles of Drug Delivery to the Respiratory Tract", *Drug Delivery to the Respiratory Tract*, Ganderton, D., and Jones, T., ed., Horwood, London (1987). Padfield concludes "The design of delivery system for administering drugs to the lung can have as much, or more, impact as the choice of drug." (id.) Previous attempts to improve the effectiveness of aerosol medicine inhalers include a number of devices including spacers, aerosol holding chambers, flow-activated triggering mechanisms, and dry powder generators.

The problem of medicine deposition in the mouth and throat can be alleviated in some cases by the use of a tube spacer, an extension tube inserted between the metered unit-dose inhaler and the patient's mouth. This procedure still requires coordinated patient action and in itself provides no feedback to the patient as to the success or failure of the overall effort.

Another approach to improving MDI usage is the use of chambers or reservoirs into which the aerosol is discharged prior to inhalation. Such devices reduce the need for coordination of actuation and start of inhalation. A widely used device is described in Sackner, et. al., U.S. Pat. No. 4,484,577, 1984. This device also provides an audible whistle when the inspiration rate is above a fixed level. The device fails to address inter-patient variations in correct inhalation patterns, as well as the breath-holding stage. A common drawback of all chamber devices is their bulk. Such devices may not fit conveniently in a pocket or purse, and many patients are unwilling to use such large devices due to self-consciousness. The process in accordance with the present invention can be used irrespective of whether a tube spacer or a reservoir is used.

Conventional systems also include several inhaler devices which address the coordination problem by incorporating a means of triggering the medication release by the start of inhalation. Such devices have been described by Wass, U.S. Pat. No. 4,664,107 1987, and Johnson et. al., U.S. Pat. No. 4,803,978 1989. Shaner, U.S. Pat. No. 4,739,754, 1988 describes a "Suction Resistant Inhaler" whose design fosters a deep inhalation by the patient.

Other conventional devices have incorporated electromechanical components in order to record the timing and date of usage for review by a healthcare professional. Spector, et. al., "Compliance of Patients with Asthma with an Experimental Aerosolized Medication: Implications for Controlled Clinical Trials," *Journal of Allergy & Clinical Immunology*, 77:65-70 (1986) discloses the use of a nebulizer chronolog to record the patients' usage of MDIs between clinic visits. This incorporates a device for recording the time and date of each canister actuation for later review by physicians conducting research on patterns of patient compliance. This device lacks the capability for obtaining any information regarding the inspiratory maneuver itself. Furthermore, since the intention of the study was to record patients' MDI usage patterns without their knowledge, the device not provide any feedback to the patients regarding proper inhalation technique.

Similar devices are described by Rand et al., U.S. Pat. No. 4,817,822, 1989, and Dessertine, U.S. Pat. No. 5,020,527, 1991. The Rand device incorporates a mechanical rachet wheel and driving member to drive an indicator of the number of actuations of an aerosol canister. The Dessertine device provides a timer and a counter for tracking the number of and time between actuations.

In the aforementioned devices the time course of air flow is not measured, nor is it compared to the desired pattern for the specific patient as may be determined by a healthcare professional. Thus, these devices address only the aspect of compliance relating to if and when the medicine was used. In order to assess whether an aerosol medication has been used effectively, it is necessary to further determine information regarding the patient's coordination of actuation and inspiration, volume and flow rate of inspiration, and post-inspiratory breath holding.

In summary, conventional devices fail to adequately address the need for immediate patient feedback regarding multiple steps in the correct use of inhalers. These devices are also inadequate in providing information to both patient and healthcare professional regarding the critical factors which determine the success of medicine delivery, including coordination of inhalation with actuation, inhalation flow rate and duration of breath holding.

What is needed is a hand-held inhaler device which can monitor the complete time course of airflow during an inhalation, and which possesses the capability to guide the patient in its correct usage before, during, and after use. What is also needed is such an inhaler whose functions include the capacity to record relevent information about the timing and nature of its use for subsequent review by a healthcare professional.

SUMMARY OF THE INVENTION

The present device detects how much air is inhaled through the inhaler with what time course (including such derived measurements as how much volume is inspired within the bounds of a given flow range) as well as certain events such as the triggering of the release of aerosol. The system can be set up to compare the resultant time course to either (a) a standard target envelope (e.g., one or more of flow, volume, and time) for that medication or (b) a specific target envelope for that particular patient programmed into the intelligent inhalation device by a healthcare professional. Based on the comparison, the success or failure of effective inhaler actuation and aerosol inspiration can be signaled to the patient (e.g., visually or through sound) and may be recorded with a time and date stamp for later decoding and evaluation by a suitable healthcare professional. In a preferred embodiment of the invention, the device would also possess the ability to signal the patient to continue post-inspiratory breath holding, and record the end of breath holding for use in interpreting the success of medication delivery.

In addition, immediate feedback can be supplied to the patient as to the specific nature of any mistakes made. For example, a message might be given that the patient's inhalation was too rapid.

In a preferred embodiment of the invention sufficient memory is provided to store data from a large number of inhalations. This automated record may be used in conjunction with a manual log kept by the patient (e.g., what event, such as exposure to an allergen, caused the need to administer the medication) or in a semiautomated fashion by having the patient or attendant encode event-related information into the inhaler device memory. An example of the latter would be the pressing of a button in a certain pattern that would be associated with a specific event. This event information would be stored together with a time and date stamp.

In an alternate embodiment of the invention, the inhaler device would possess the capability to signal the patient at the times for which its use has been prescribed. This signal could be provided by means of indicator light(s), audible beeps or tones, vibration of the unit, or some combination thereof. Timing of such signals would be programmed in accordance with standard or patient-specific prescriptions for usage.

In another alternate embodiment of the invention, the inhaler device would be integrated with a holding chamber (reservoir) into which the aerosol is released prior to inhalation. The interior volume of this chamber would be large enough to allow for the expansion of the aerosol. Electronic functions remain the same as those provided in the non-chamber device.

DETAILED DESCRIPTION

Figure 6A:
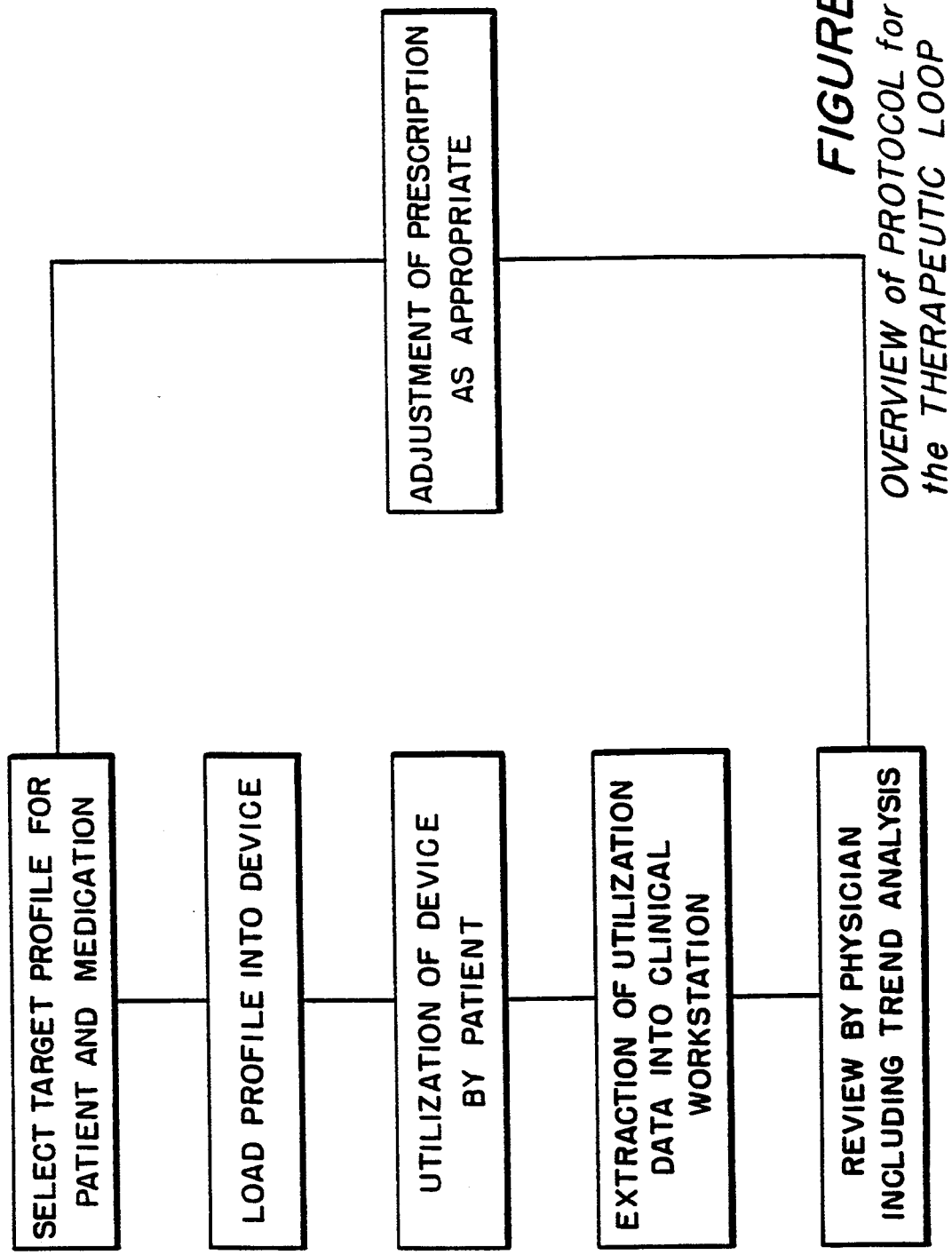
FIGS. 6A and 6B are flow charts showing the overall processes for use of the intelligent inhaler by healthcare professional and patient.

The overall process of the present intelligent inhaler system is shown in FIG. 6A which provides an overview of the protocol for closing the therapeutic loop. The target profile envelope is selected and inserted (e.g., via a clinical computer-based workstation). This target envelope is (a) a generic pattern, or (b) a tailored time course based on the patient's individual spirometric values or other input, as appropriate. The device is used by the patient and at the next visit to the physician's office, the utilization data are extracted and transferred to the clinical workstation where they are reviewed by the physician or other healthcare professional including analysis of trends with respect to previous periods. The prescription is adjusted if and as appropriate and, if necessary, a new target profile for the given patient and medication is loaded into the intelligent inhaler device.

Figure 6B:
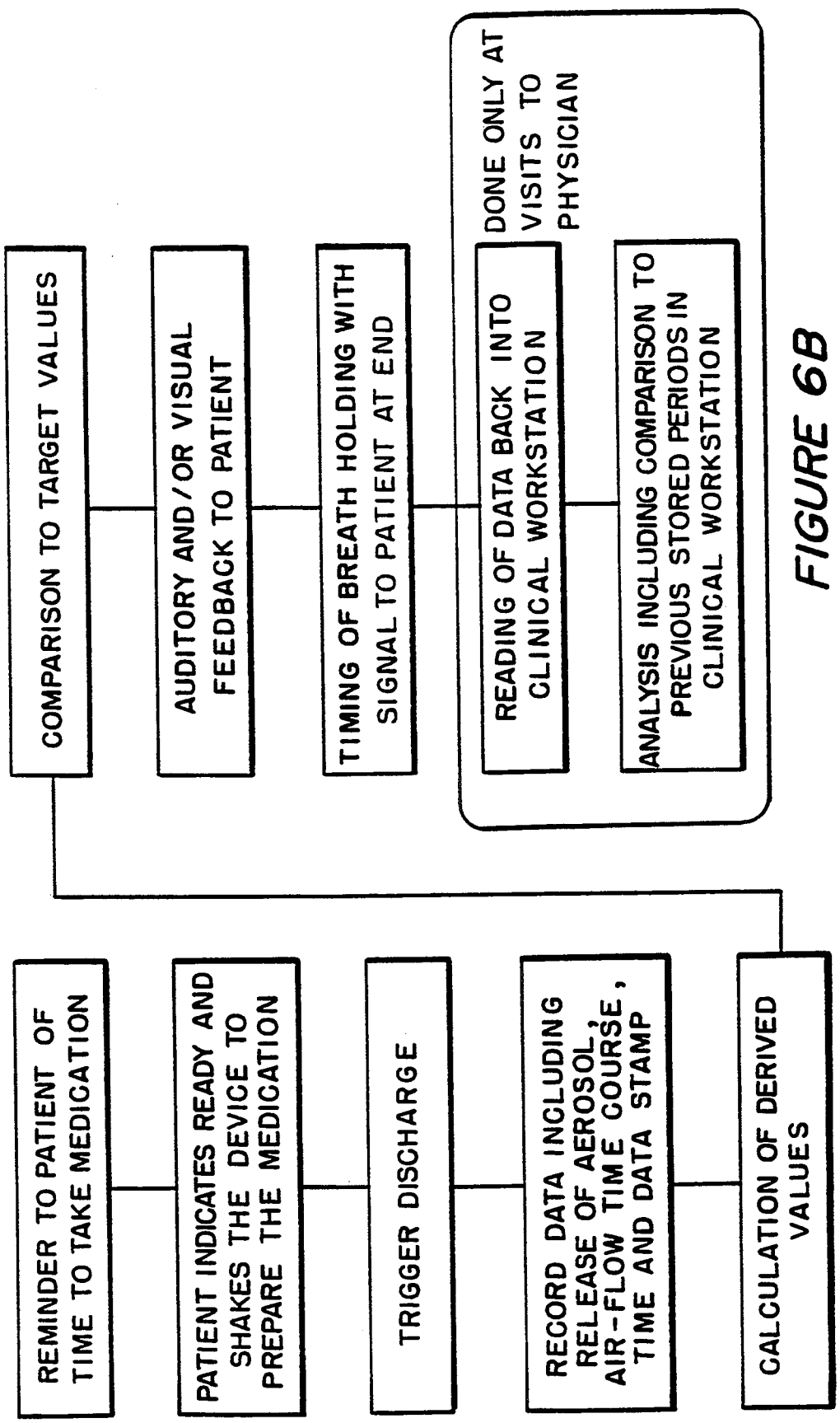

FIG. 6B is an overview of the process for utilization by the patient. Initially, the device reminds the patient that it is time to take the medication. This is used for medications, such as corticosteroids, which are taken over long periods of time rather than in an immediate reaction to an acute event such as an asthmatic episode. The device is then turned on and the release of aerosol triggered.

Recording of data begins at the start of inspiration or upon actuation of the medication canister, whichever is earliest.

The actual time course of each inhalation is compared to the objective target time course, a comparison derived, and a signal given as to success or failure. At the end of inhalation, a timer is started which runs for the period of time during which the patient should hold his or her breath. At the end of ten seconds (or other period as specified), an auditory and/or visual signal is supplied to the patient. The patient can press a button to signal when breath holding actually ended. In an alternate embodiment, the patient can signal that event by exhaling (at least initially) back into the hand-held device with the time recorded when an increase in air flow above a specified threshold is detected.

In addition, suggestions for corrective action (e.g., hold breath for a longer time) can be given.

Recorded data are stored for later readout into a recordkeeping device (such as a computer-based clinical workstation in a physician's office) for interpretation and perhaps comparison to other time periods by a healthcare professional.

Figure 1:
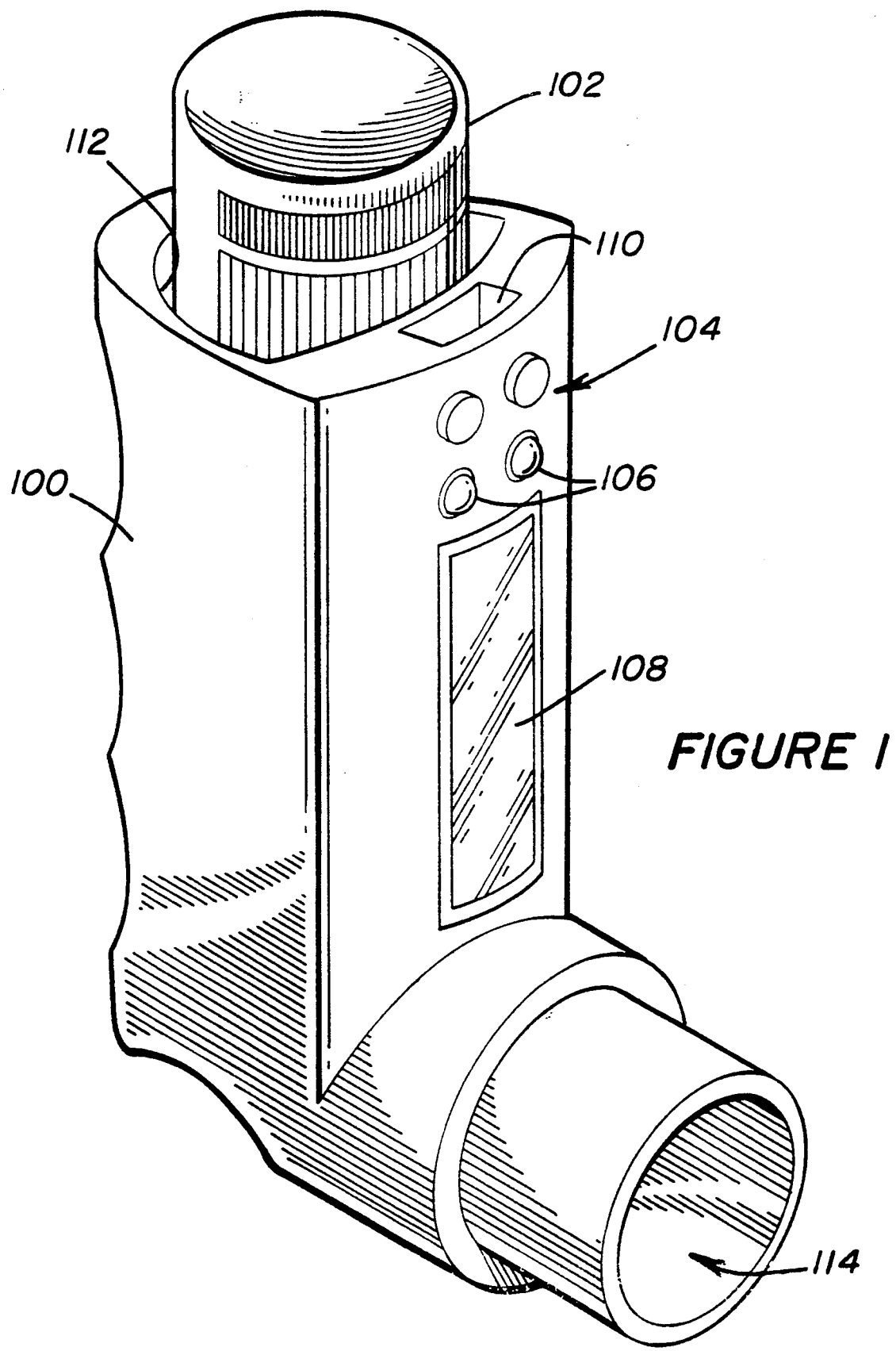
FIG. 1 is an oblique side view of the present intelligent inhaler device.
Figure 2A:
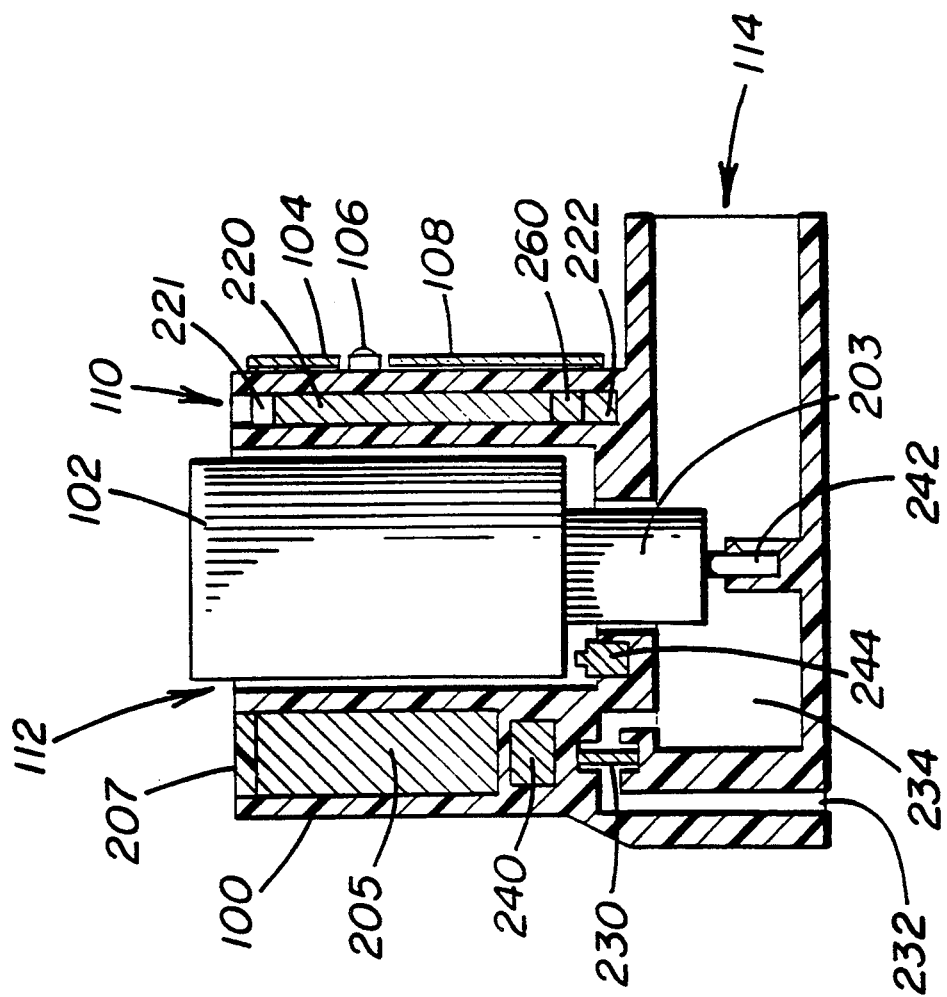
FIG. 2A is a side sectional view of the mechanical construction of the device illustrating major components including the incorporation of the type of pressurized canister most widely used for dispensing metered doses of aerosols.

An external view of the preferred physical embodiment is shown in FIG. 1. Located in the housing 100, is a pressurized medication canister 102. An important feature is the ability to insert and utilize standard metered-dose inhaler canisters, although the device can be modified to support other containers as appropriate. Communication with the patient occurs with input through push-button switch means 104, and output through LED indicators 106 and LCD panel display 108. Communication to and from the clinical workstation in the office of the physician is through input/output data communication means 221 as shown in FIG. 2. While this is shown as a simple I/O data connector socket in FIG. 1, the invention is not so limited. The data communication means 221 in FIG. 2A also is intended to include a compact transceiver means for communicating with a spatially remote control source, such as a workstation, through a radiofrequency communication channel, or the like in accordance with well known techniques. The remote workstation is capable of receiving transmission of data such as the time of actual usage or the inhalation pattern. The present device is also capable of being reprogrammed by the remote workstation to alter the dosage or to provide specific feedback to the patient as to corrective action.

Air to be mixed with the aerosolized medication enters from the opening in the top of the inhaler housing 112, and the patient's inspiration pulls the air and aerosol mixture through mouthpiece 114.

A mechanical construction diagram of a preferred embodiment of the device is shown in FIG. 2A. The "on" switch 104 for the device turns on the power in the battery 205 (which is physically accessible through cover 207) for circuits which are not active between times of inhaler usage. Other circuits may be powered at predetermined times, and power is supplied continuously to circuits responsible for maintaining the contents of memory. The Application Specific Integrated Circuit (ASIC) 220 contains the microprocessor, memory, calendar/clock, power controller, LED/sound driver, LCD driver, input/output interface, button-switch interface, and analog to digital converter. The electronics are connectable to a workstation by a conventional connector means 221. Whether the device has been shaken properly is determined by input from motion sensor 222. Flow is measured utilizing a flow measuring means or flow meter (comprised of elements 232, 230, 234 and 112) as follows. Differential pressure is measured through pressure sensor diaphragm 230 which is connected by flow channels 232 to both outside atmosphere and interior flow chamber 234. Pressure-sensor diaphragm 230 is connected to the pressure-sensor electronics 240 which are interfaced to an analog to digital converter on ASIC 220. Aerosolized medicament is released when the medication canister 102 is depressed and its valve 203 is opened with the pressurized liquid being discharged through the atomizer 242. An actuation pressure switch 244 is disposed for contact with canister 102 when the canister is depressed to discharge a unit of medicine through atomizer 242.

Figure 2B:
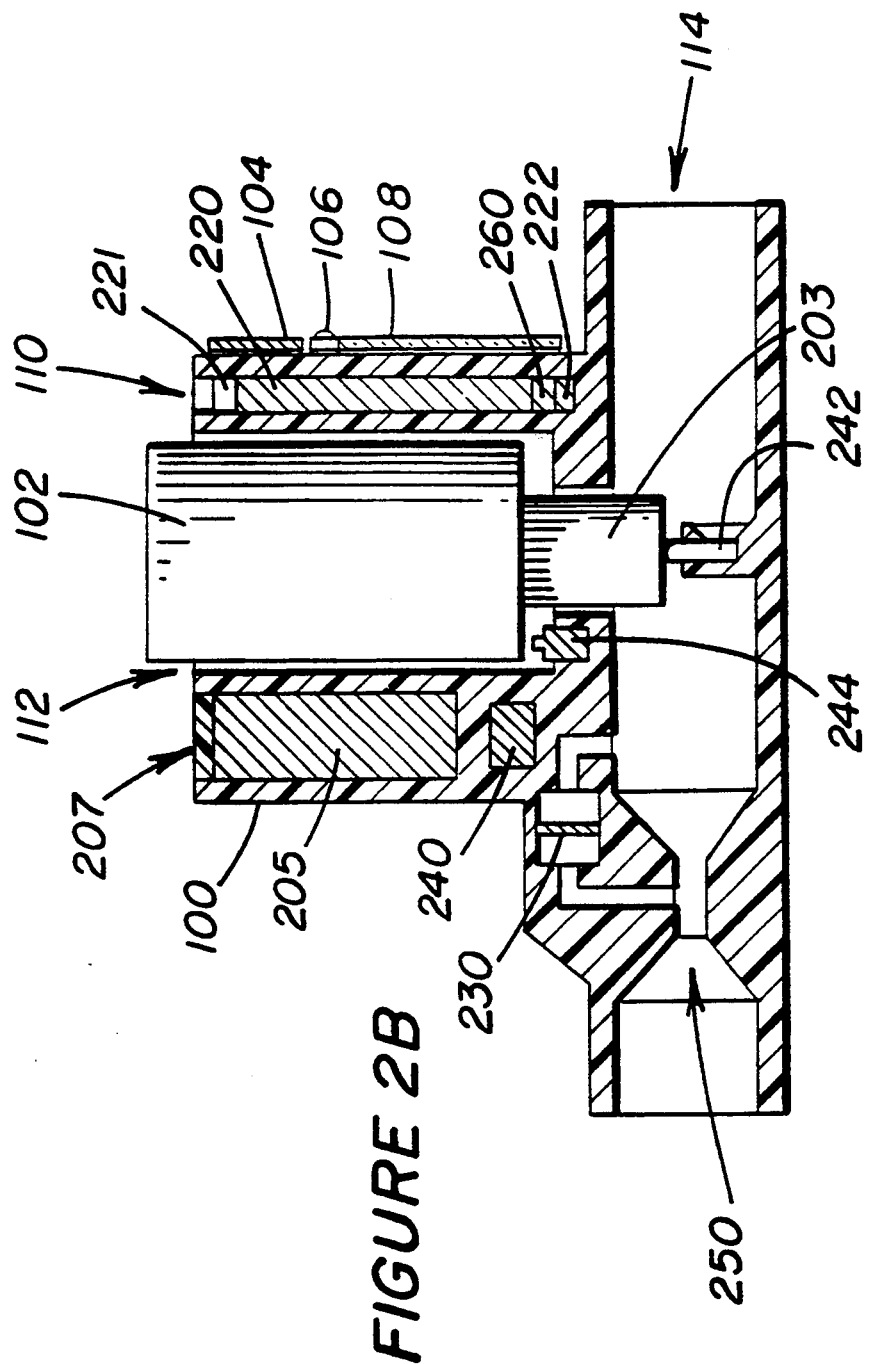
FIG. 2B is a sectional view of an alternate mechanical construction incorporating a Venturi-type flow meter.

FIG. 2B illustrates an alternative embodiment utilizing a venturi flow meter design. This construction is the same as in FIG. 2A except that the linear response of pressure sensor diaphragm 230 is proportional to flow through the Venturi flow meter 250, with the signal transmitted by the pressure sensor electronics 240. This implementation provides the ability for the patient to exhale (at least initially) into the device to indicate the end of the breath-holding period. The exhalation would be into the input port 112 to avoid clogging the atomizer 242. This port 112 could be used for recording the patient's maximal exhalation or other spirometric measurements. The form of pressure sensor is not critical. A semiconductor pressure sensor might be directly incorporated into an ASIC device [Wise, K. D., and K. Najafi, "Microfabrication Techniques for Integrated Sensors and Microsystems," *Science*, 254:1335–1342, (1991)]. Alternatively, a different means for measuring air flow such as a miniaturized mass-flow sensor, could be employed.

Figure 3:
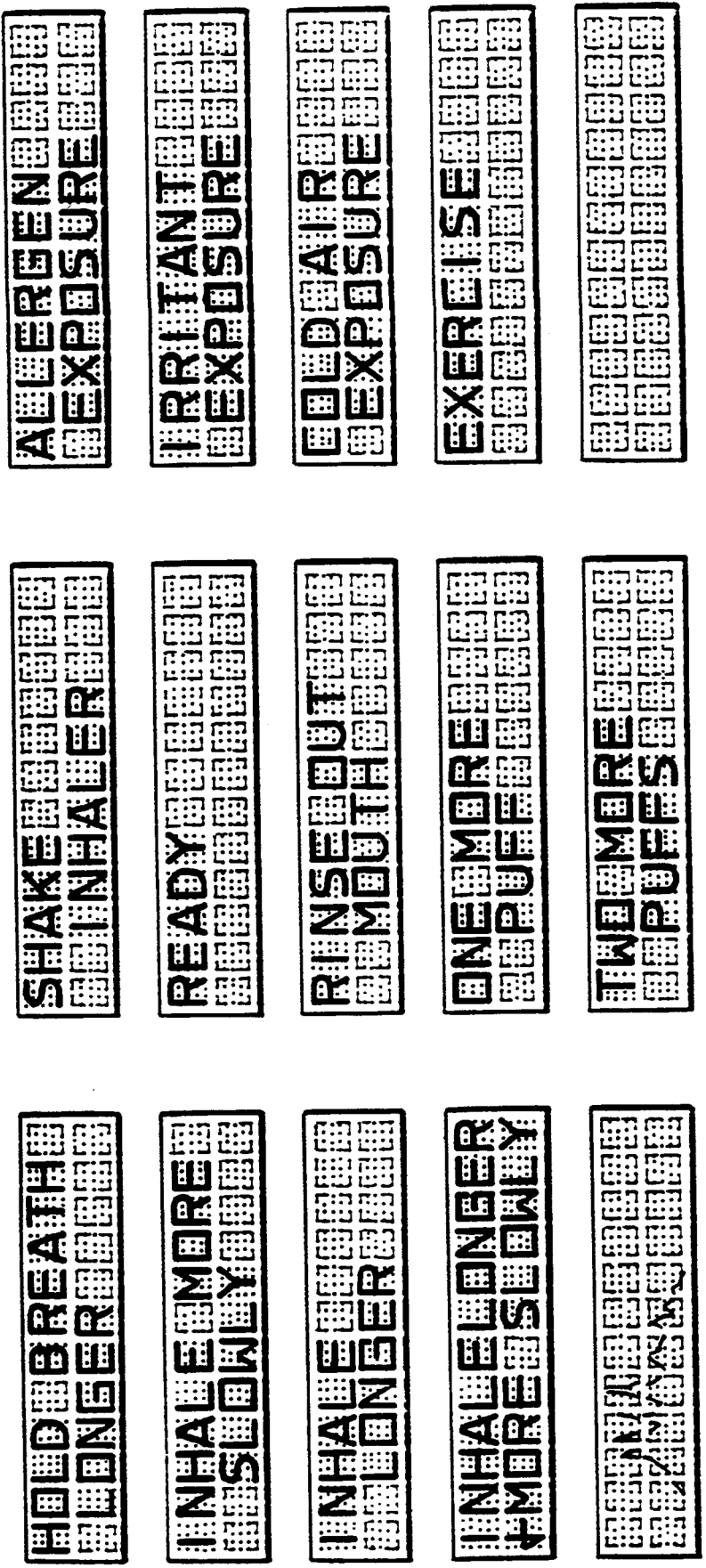
FIG. 3 illustrates typical messages and graphic output supplied to the patient or attendant by the device.

FIG. 3 shows a set of sample messages to the patient. Feedback regarding individual inhalation efforts appears in the left column, including an illustration of the time course of inspiration relative to a target range. General instructions are shown in the center, and prompts for event recording are shown on the right. These messages are displayed by the LCD panel 108 as shown in FIG. 1. Auditory output comes through the Piezo sound generator 260 as shown in FIG. 2A and 2B.

Figure 4:
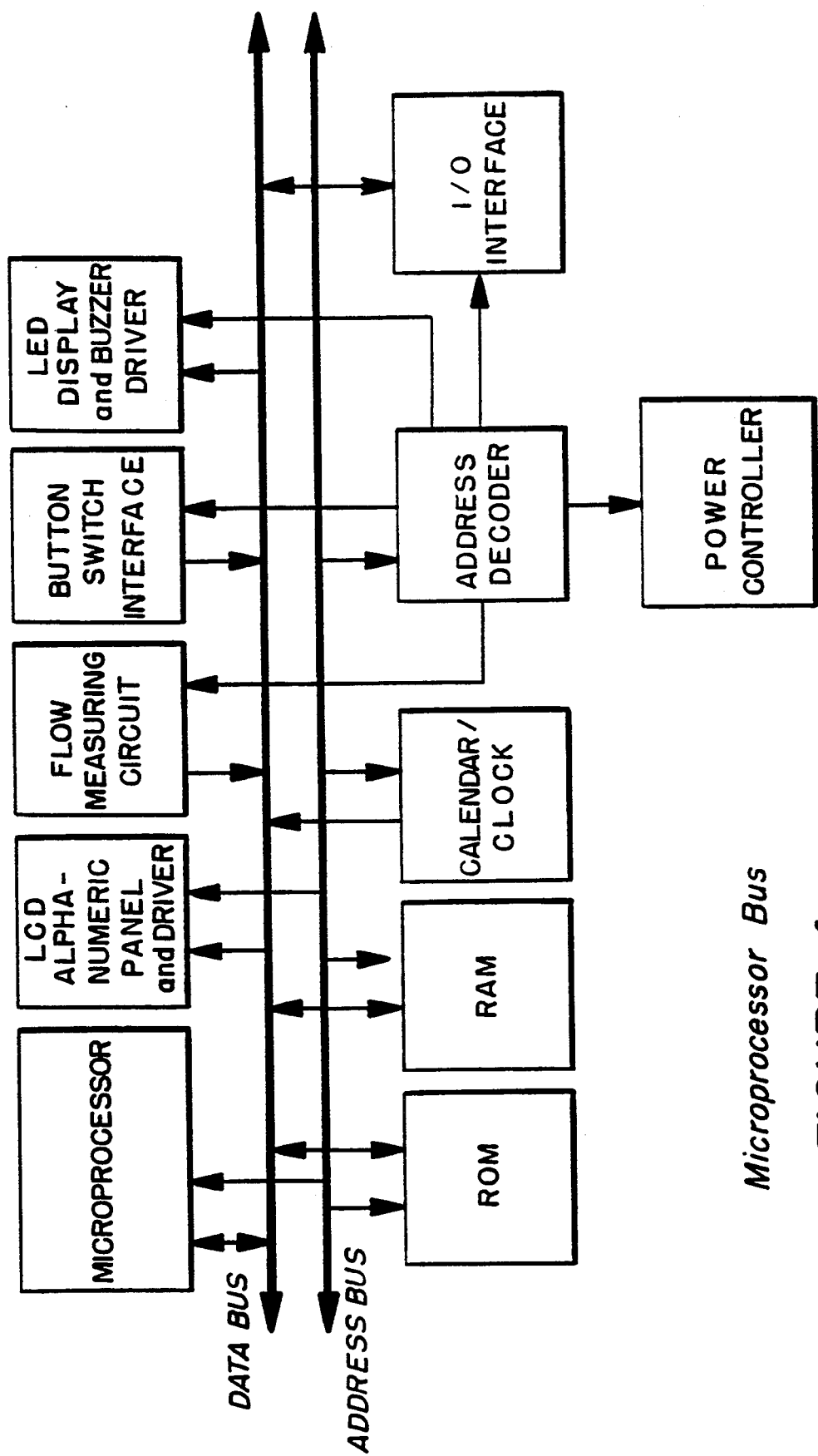
FIG. 4 is a block diagram of electronics illustrating the overall architecture of the intelligent inhaler device

FIG. 4 shows a block diagram of the system. In a preferred embodiment, many of the electronic elements are incorporated within application specific integrated circuit (ASIC) 220, including the microprocessor, RAM and ROM storage, calendar/clock, A/D converter, I/O functions, and drivers for LCD, sound, and LED devices. However, in various implementations of the invention these functions may be distributed on multiple integrated circuits, including standard and/or custom devices. The scope of the invention is not limited to any single specific implementation.

The microprocessor memory requirements are supplied by the Random-Access Memory (RAM) and the Read-Only Memory (ROM) modules. The calendar/clock module provides the ability to signal to the patient when it is time to take the medication, and generates time and date stamps for each inhaler use. The analog input signal from the pressure-sensor electronics is transformed by the analog to digital converter. The power controller provides power to all the device subsystems including the microprocessor and associated components, flow-measuring circuit, LED/sound display and driver, and the LCD alpha-numeric panel and driver. Input/output circuitry handles signals coming into and/or going out of the push-button contact switches and two-way communications with the computer-based clinical workstation or other suitable device occurs through the external communications connector 221.

Figure 5A:
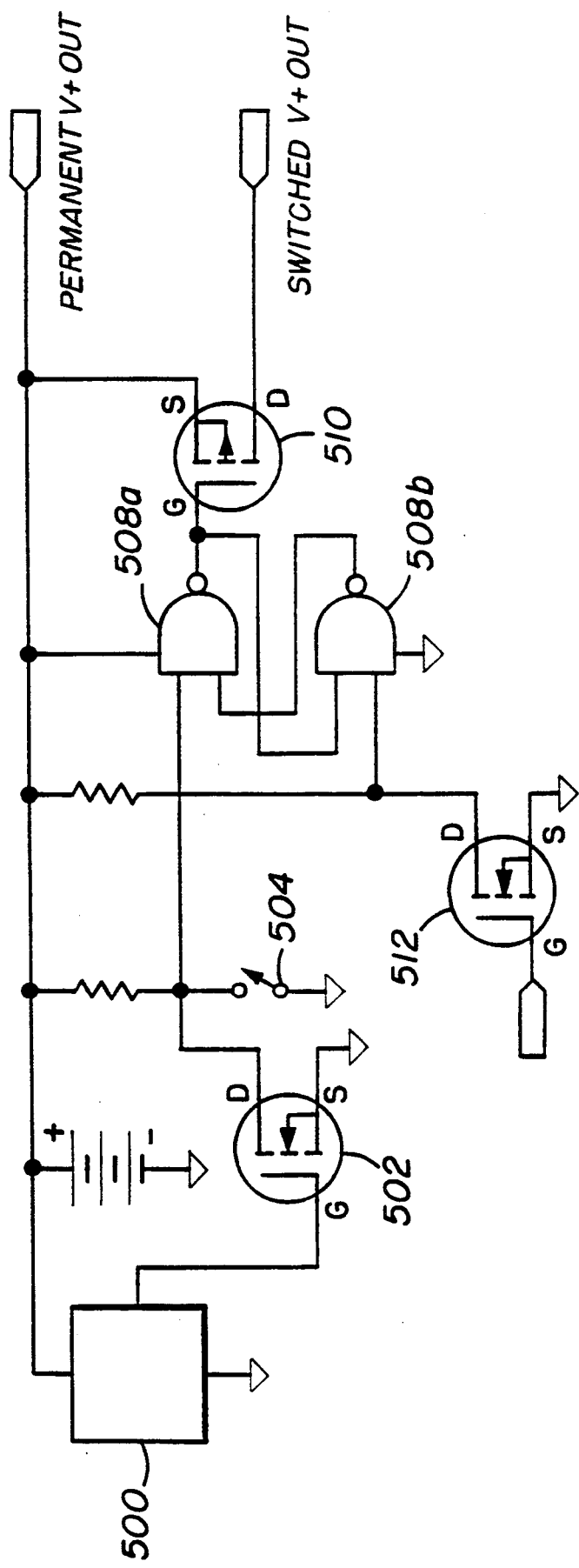
FIGS. 5A through 5E show the circuit diagrams for subsystems of the device.
Figure 5B:
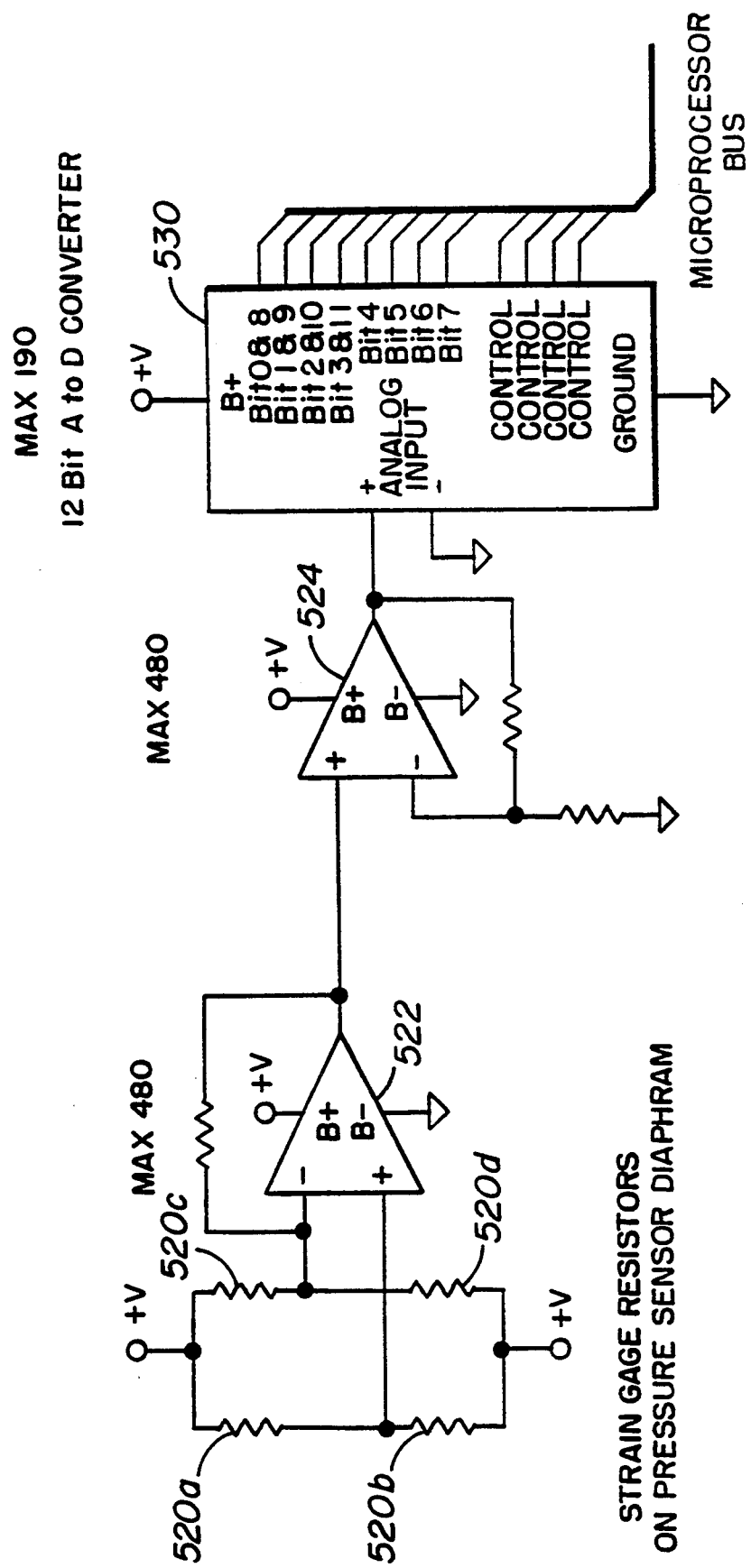

FIGS. 5A through 5B illustrate subsystem circuit diagrams. FIG. 5A shows the power control circuit. Modules such as the RAM are powered continually. As to power control, when the motion sensor 500 is triggered with transmission through the MOSFET semiconductor 502 on the left or the "on" 504 button switch closed, the NAND 508a, 508b gates change state and switch on the MOSFET semiconductor 510 on the right to provide voltage to the microprocessor. When the microprocessor goes into the "sleep mode" after its operational sequence, it transmits an "off" signal to the MOSFET semiconductor 512 which deactivates the NAND gates 508a, 508b and shuts the system down. The device is battery operated using preferably a lithium battery for long life.

FIG. 5B shows the pressure-sensor flow-meter electronics. The strain gauge resistors 520a, 520b, 520c and 520d in the bridge circuit are located on the pressure-sensor diaphragm 230 which measures the pressure differential in the flow meter comprised of elements 232, 230, 234 and 112 in FIG. 2A or in the Venturi flow meter 250 shown in FIG. 2B. In accordance with techniques which are well known to those skilled in the art, an analog signal is generated through the two stages of operational amplifiers 522, 524. This signal is transformed by the analog-to-digital converter 530 and fed via a bus to the microprocessor (not shown).

Figure 5C:
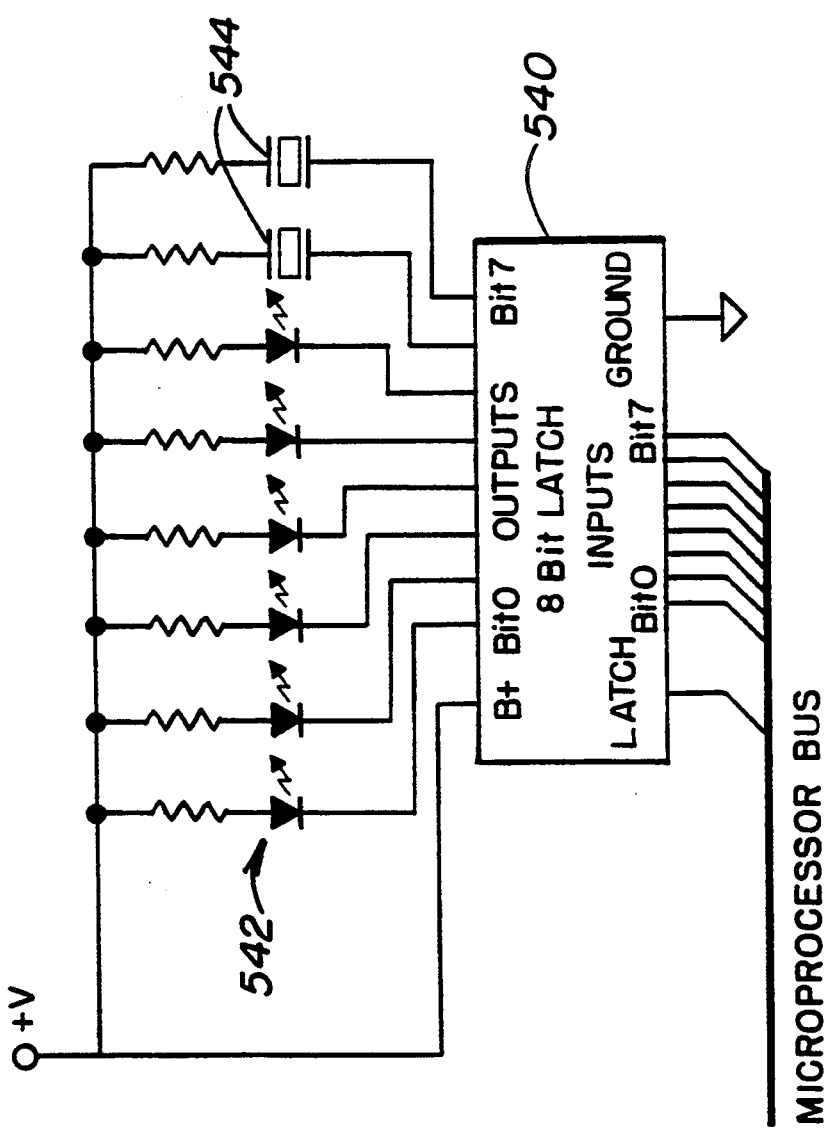

FIG. 5C illustrates the LED/sound display and driver. The control signal comes from the microprocessor to 8 bit latch 540. The control signal is stored by the 8-bit latch 540. Selected components, such as zero to six of the LEDs 542 and zero to two Piezo sound generators 544 are turned on. In like manner, components which are on can be turned off with a subsequent control signal transmitted by the microprocessor.

Figure 5D:
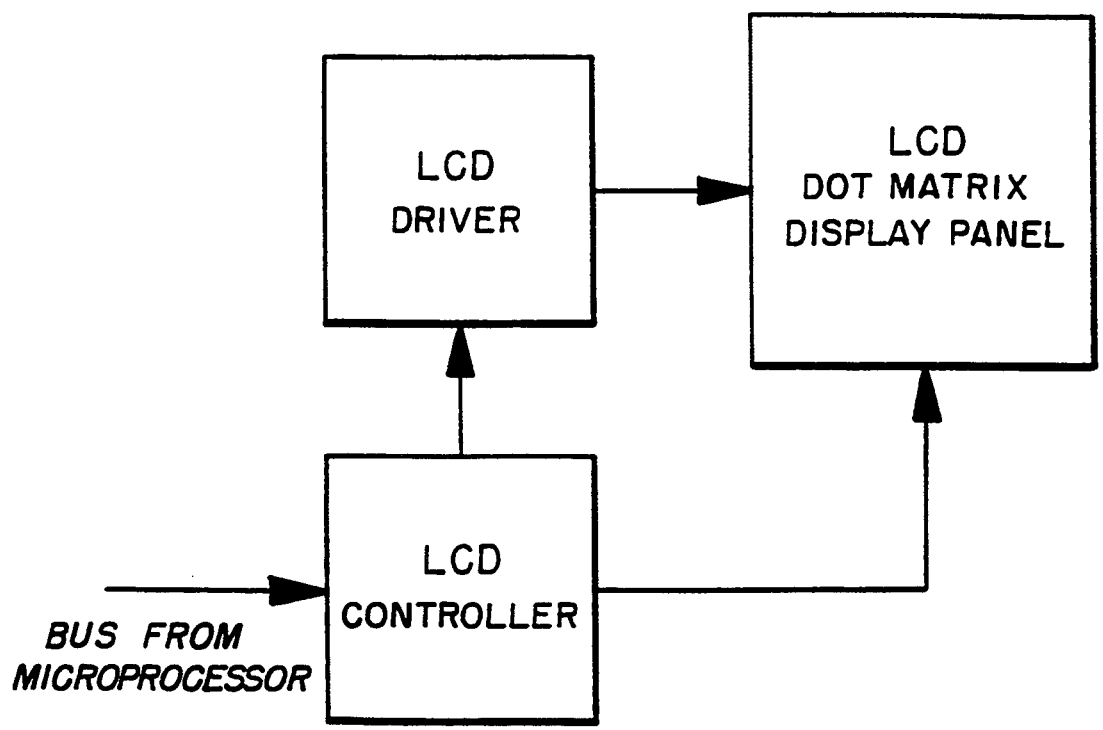

FIG. 5D presents the block diagram for the LCD alpha-numeric panel and driver. The control signal comes in over the bus to the microprocessor and the LCD controller provides input to the LCD driver (input to rows of display) and the LCD dot-matrix display panel (input to columns of display) in accordance with techniques which are well known.

Figure 5E:
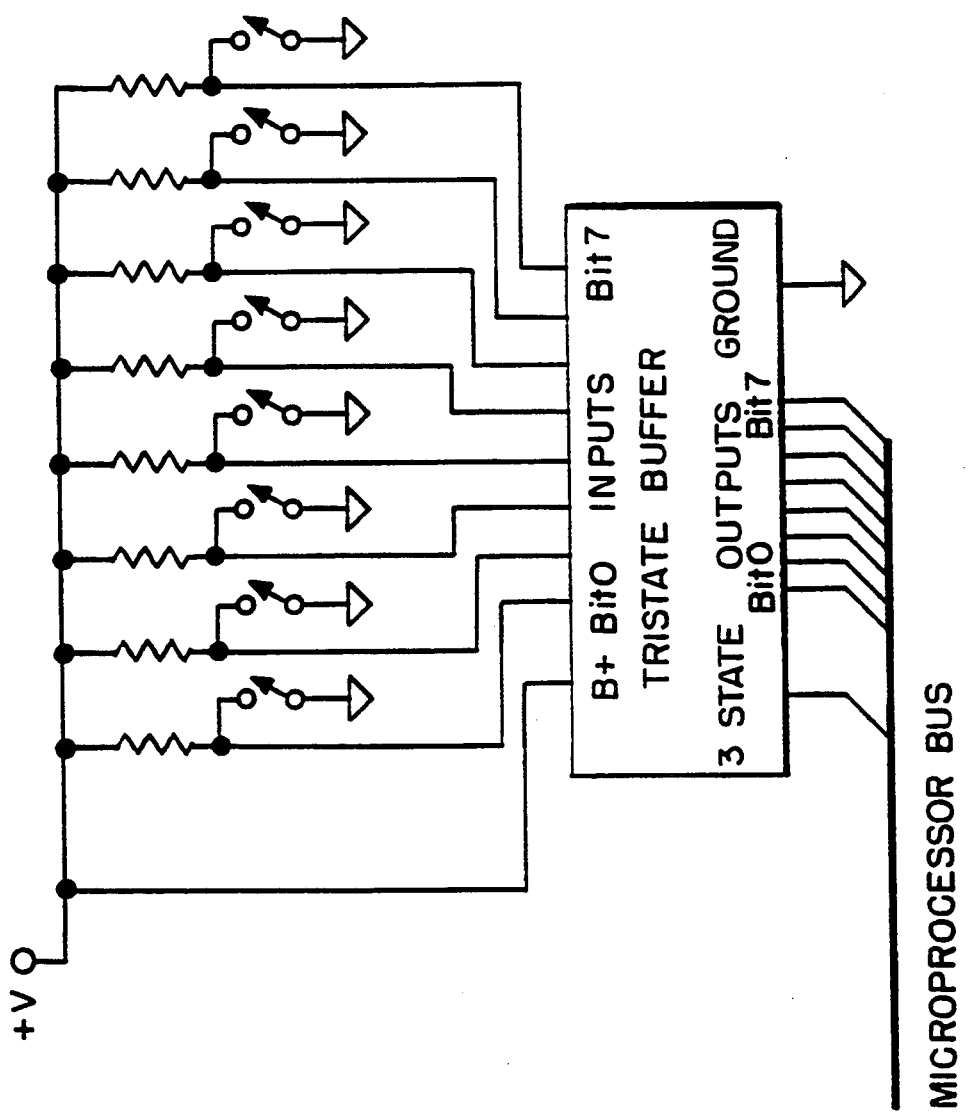

FIG. 5E illustrates the pushbutton switch interface. Because this interface resides on the microprocessor bus, a three state buffer is used (off, floating, on). In the figure, the term tristate is used, reflecting a particular version of the buffer produced by National Semiconductor Corporation. The current status of each of the push-button switches is held within the buffer. The three-state buffer is interrogated by the microprocessor by turning the three state control to "on" and the status of each line ("on" or "off") is transmitted from the three-state buffer back to the microprocessor over the microprocessor bus.

FIG. 6A shows the overall protocol whereby data collected by the intelligent inhaler are used to close the therapeutic loop, and enable the healthcare provider to track the patient's medication use between visits. The physician selects the target profile for the patient and medication. The profile is loaded into the device and the device is used by the patient. At the next visit of the patient to the healthcare provider, the data related to patient utilization of the device is extracted and moved to the clinical workstation. The data are then reviewed by the physician and trend analysis can be done, not only within the given set of data, but in comparison to previous periods. An adjustment can be made to the prescription if the physician chooses to do so. If there is a change, the new prescription information and/or target profile are loaded into the intelligent inhaler device.

FIG. 6B illustrates the process of utilization of the intelligent inhalation device by the patient. If the medication is taken at prescribed intervals rather than on an episodic basis, a reminder of the time to take the medicine is signalled to the patient. The patient depresses the "on" switch to indicate the medicating sequence is to be started and shakes the device with the canister inserted so the medication is adequately prepared for discharge. Depression of the canister enough to discharge the medication is the trigger event. Recording of the data, including release of aerosol, air-flow time course, and associated time and data stamps ensues. Derived values are calculated and compared to the target values of the target function. The breath holding period is timed and an auditory and/or visual signal supplied to the patient at its end. Auditory and/or visual feedback is provided to the patient as to success or failure of the inhalation actions including text messages as to what corrections are appropriate (e.g., INHALE SLOWER). At the next patient visit, the recorded data are read into the host clinical workstation and the data analyzed and displayed, including trend analysis in comparison to previous periods.

A typical cycle of operation, with reference to FIGS. 1, 2A and 2B, is as follows:

If the medication is to be taken regularly, the time for the medication to be taken can be signalled through Piezo sound generator 260 and/or LED display 108.

The unit is held in patient's hand such that mouthpiece 114 faces the patient.

The patient presses pushbutton switch 104, activating the "on" switch to close and activate the microprocessor and associated functions.

The patient shakes the unit per instructions, causing the motion sensor 222 to generate a signal for storage in the memory contained in the ASIC 220. If the on switch 104 has not yet been activated, motion sensor 222 causes the unit to turn on just as if the on had been closed. Optionally, this signal also prompts indicator lights 106 to turn on as well.

Patient then places the mouthpiece 114 in mouth, depresses medication canister 102 firmly enough to cause metering mechanism 203 to discharge a unit of medicine through atomizer 242, and the patient simultaneously begins to inhale. Depression of the canister 102 causes closure of actuation sensing switch 244 and transmission of a signal for this event to microprocessor within the control electronics of ASIC 220.

With the inhalation, aerosolized medication flows through the mouthpiece 114 into the mouth of the patient.

Pressure-sensor diaphragm 230 senses air flow coming through the upper housing opening 112 and moving through flow chamber 234 by measuring the pressure differential between the outside air through passage 232 and the internal chamber 234 (in the configuration shown in FIG. 2A). In the alternate construction shown in FIG. 2B, pressure sensor diaphragm 230 senses air flow by measuring the pressure differential between the two stages of Venturi flow meter 250. Pressure-sensor electronics 240 generates a signal representative of flow rate to the analog-to-digital converter contained in the ASIC 220.

The analog-to-digital circuitry converts this signal to digital form, upon which it is stored as a series of (e.g., 8-bit) samples in a RAM contained in the ASIC 220.

As patient continues to inspire, time series flow samples in memory are compared with target objective profile representative of correct inhalation technique also stored in RAM contained in ASIC 220. The microprocessor contained in ASIC 220 performs the comparison of actual versus target values and depending upon the results sends signals to indicator LED's 106.

Upon completion of inspiration, cessation of flow is detected and measurement of time duration of breath hold begins using the calendar/clock module contained in ASIC 220.

Upon end of breath hold, patient presses push button 104 which sends an event signal to microprocessor in ASIC 220 for storage in RAM and calculation of breath-holding duration.

Results of the maneuver, including breath holding performance are used to select textual or iconic feedback from a table stored in RAM contained in ASIC 220, in accordance with techniques which are well known for display to patient via LCD display panel 108. Note that text table can consist of multiple sections corresponding to differing languages.

After the inhalation maneuver is complete, the device can pose questions to the patient on LCD display 108 and answers such as "yes" or "no", or other answers corresponding to the number of times the push button switch is activated are input by the patient through push-button switch 104.

After a specified time (long enough to permit an additional discharge of medication if there is to be one) an output signal from the microprocessor to the power control circuit causes the system to return to sleep mode.

Data from multiple maneuvers can be downloaded subsequently through connector 221 into a clinical workstation or similar device for review by professional including trend analysis within the set of just downloaded data and comparison to previous periods.

Upon downloading of data, records for individual maneuvers are erased from the RAM contained in ASIC 220, and battery 205 is checked for charge.

The site of compliance monitoring includes a digital computer means (not shown) for communicating electronically with the microprocessor means 220 incorporated in the programmable inhaler. The digital computer means at the monitoring site includes means for monitoring and improving a patient's medication compliance with the use of the handheld inhaler. The monitoring computer is linked with transmission means for remote electronic retrieval of the data measured by and stored in the inhaler microprocessor through data communication techniques which are well known, such as radiofrequency, optoelectronic communication, or the like.

The monitoring computer is programmed to evaluate the data received from the inhaler microprocessor means and to provide interpretations of the effectiveness of compliance efforts based on the retrieved data. The monitoring computer also includes a display means for meaningful display of the compliance data. Such a display means preferably includes patient's projected target envelope for maximized delivery of medication as compared to the actual, measured performance of the patient.

It will be appreciated by those skilled in the art that there are a multitude of methods for programming the monitoring computer to achieve the evaluation of a patient's medication compliance parameters which will maximize delivery of medication to the large airways, small airways, alveoli or any part of the respiratory tract. Thus, the present method is not intended to be limited to a specific software implementation for diagnosing a patient's projected compliance as a target envelope of values and for measuring the actual performance of the patient with respect to the target envelope.

In a preferred embodiment, the monitoring computer includes software which is readily programmed by one skilled in the art to utilize data input from diagnostic instruments, diagnostic tests, clinical records, clinical observations, professional opinions, or the like in calculating a target envelope of inhalation parameters which will maximize the delivery of aerosolized medication to any selected part(s) of the respiratory tract of a particular patient, or to indicate other changes in therapy such as type of medication. The foregoing data include quantifiable parameters relating to the physical condition of the airways of a patient, such as the size of the patient's air passages.

The data are input into the monitoring computer as a table of values, or physical parameters indicative of the condition and capacity of a patient's air passageways and inhalation characteristics. The table of physical parameters are then mapped to provide the target envelope of values, which if matched by the patient's performance, will maximize the distribution of the aerosol medication any selected parts of the respiratory tract. The monitoring computer compares the patient's actual measured performance to the target envelope. The monitoring computer then communicates electronically with the microprocessor in the inhaler, and as a function of measured compliance parameters, reprograms the microprocessor, if necessary, with different target inhalation profiles, dosage levels or actuation event times that will bring the patient's performance within the target envelope and maximize the therapeutic response.

The advantages of the system described herein over conventional devices may be summarized as follows:

(a) the incorporation of both monitoring and recording the patient's inhalation time course and related events in a medicine inhaler device small and aesthetically pleasing enough to be used during normal day-to-day activities, (b) the ability to load in a target-performance envelope for one or more inhalation time/value courses and/or one or more selected variables (such as peak-flow rate) or to designate a specified generic curve, (c) the ability to sense whether the device has been shaken properly prior to discharge of a dose of aerosol, (d) the ability to provide immediate feedback both during the inhalation and afterwards as to where the patient's performance fits relative to the target-performance envelope and whether and when inhalation values fell outside that envelope, (e) the ability to provide feedback to the patient as to what corrective action, if any, should be taken, (f) the ability to provide a signal to the patient prompting him or her to continue breath holding, (g) the ability to have the patient record the timing of the end of the breath-holding period, (h) the ability to store any of the data obtained, (i) the ability to download longitudinal results from the Intelligent Inhaler into a healthcare workstation or similar device, and (j) the ability for the healthcare professional to review a patient's medicine usage for the entire period between office visits, and therefore review trends in the patient's condition in the context of a detailed historical record of the actual delivery of medication to its target sites of action in the lungs.

It should be noted that all of the above capabilities would not necessarily be included in every implementation of the system.

The device and method described here are not limited to usage with any one pharmaceutical. They may be used with locally acting respiratory drugs including bronchodilators, corticosteroids, anticholinergics, antibiotics, and others, as well as with systemically acting drugs. Differing compounds may require variations in prescribed usage, including changes in the inspiratory flow pattern. Such patterns may be chosen in order to direct the concentration of drug deposition at different sites within the respiratory tract, or compensate for variations in patient's airways morphology due to disease or trauma.

What is claimed is:

1. A portable hand-held inhaler device comprising:
a housing adapted to be hand-held by a user;
a canister of inhaled medication received within the housing;
delivery means incorporated in said housing for delivering a desired unit dose of said inhaled medication from said canister;
electronic sensor means incorporated in said housing for measurement of air flow through said delivery means;
microprocessor means incorporated in said housing, comprising means for storage of data including relative time of activation of said delivery means, and for storing data representative of duration and pattern of inspiration through said delivery means for each activation event;
said microprocessor means further comprising means for performing logical operations or interpretative calculations upon said data;
signaling means responsive to said microprocessor means for providing feedback to said user, said feedback expressing to the user whether the delivery of medication has been done correctly;
motion sensor means for detecting if said medicine canister is shaken prior to each activation event and for producing an output signal representative of the magnitude and duration of the shaking to said microprocessor means; and
means responsive to said motion sensor means for signaling the user that the canister of medication was not shaken prior to activation.

2. A hand-held inhaler device comprising:
a housing adapted to be hand-held by a user;
delivery means incorporated in said housing for delivering, upon activation, a desired unit dose of inhaled medication from an associated canister received in said housing;
electronic sensor means responsive to activation of said delivery means, incorporated in said housing for measuring flow of air through said medication delivery means and for producing output signals representative thereof for each activation event;

microprocessor means incorporated in said housing for storage of data including relative time of activation of said delivery means, and for storing data representative of duration and pattern of inspiration through said medication delivery means, said microprocessor being adapted to record data pertaining to each medication delivery event to thereby provide a record of medication delivery for compliance monitoring;

means operatively connected with said microprocessor for performing logical operations to optimize the patient's use of said delivery means in response to interpretative calculations upon said data;

signaling means responsive to said means for performing logical operations, for providing feedback to a user, wherein said feedback expresses to the user success in inhaled medication delivery and provides one or more recommendations for improved patent inhalation in subsequent doses; and wherein said means for performing logical operations further comprises a motion sensor means for detecting of said medicine canister is shaken prior to each medication delivery event.

3. An apparatus according to claim 2, wherein the microprocessor means further comprises means for storing a target envelope pattern representing the time course of an effective inspiration for comparison to measured inspiration patterns, whereby said comparison is used to govern feedback provided to the user.

4. An apparatus according to claim 3 wherein said canister of inhaled medication comprises a reservoir integral with said housing and adapted for storing a quantity of airborne medication.

5. The apparatus of claim 3 wherein said feedback further comprises means for displaying a target inspiration pattern as a function of time.

6. The apparatus of claim 5 wherein said feedback further comprises means for displaying a comparison of a patient's actual inhalation pattern with a prescribed target pattern.

7. An apparatus according to claim 2 further comprising:

computer monitoring means communicating electronically with said microprocessor means of said hand-held inhaler for retrieving and processing said stored data representative of duration and pattern of inspiration, said computer monitoring means further comprising a means for displaying said stored data for compliance review by a healthcare professional.

8. The apparatus as in claim 7 wherein said computer monitoring means further comprises means for processing data input from at least one of the following sources: diagnostic instruments, diagnostic tests, clinical records, clinical observations, and professional opinions.

9. An apparatus according to claim 2 wherein the microprocessor means incorporated in said inhaler housing further comprises means for reprogramming said signaling means to vary the desired dose of medication inhaled by the patient in response to said logical operations or interpretive calculations upon said data.

10. An apparatus according to claim 9 further comprising means for reprogramming the signaling means to vary the timing of frequency of delivery of medication.

11. An apparatus according to claim 2 wherein said microprocessor further comprises wireless transmission means for transmitting output signals representative of said stored data to a remotely located computer means for compliance monitoring.

12. An apparatus according to claim 11 wherein said wireless transmission means comprises input means responsive to remotely generated signals for reprogramming said microprocessor means to vary the time interval for delivering a desired unit dose of said medication.

13. An apparatus according to claim 12 responsive to a remotely generated input signal indicative of the times prescribed for delivery of said dosage of medicine, wherein said means for indicating comprises at least one of the following: indicator lights, auditory tones and vibration.

14. An apparatus according to claim 2 wherein said microprocessor comprises data communication means for transmitting said data along a communication path to a spatially remote control means for compliance monitoring and said data communication means includes means for receiving remotely generated signals from said remote control means for reprogramming said microprocessor to vary the desired dose of said inhaled medication.

15. An apparatus according to claim 2 wherein said signaling means further comprises interactive feedback means for interrogating a patient regarding exposure to an event affecting inhalation such as exposure to allergens and breathing irritants, and further comprising switch means adapted to receive a yes or no answer from said patient in response to said means for interrogating and for recording said answer as data to be stored in said microprocessor.

16. An apparatus according to claim 2 wherein said signaling means further comprises interactive feedback means for providing immediate feedback to the patient as to success or failure of an inhalation action, including a message as to what correction is appropriate.

17. An apparatus according to claim 2 wherein said interactive feedback message comprises a message such as at least one of the following: "clean inhaler", "rinse mouth", "avoid pets", and "avoid cold."

18. An apparatus according to claim 2 wherein said canister of inhaled medication comprises a reservoir of airborne medication disposed externally from said hand-held inhaler, including conduit means for communicating said airborne medication with said hand-held inhaler delivery means.

19. An apparatus according to claim 2 wherein said delivery means comprises a spacer having a first end integral with said hand-held inhaler and having a second end adapted for delivering said medication into a user's mouth.

20. An apparatus according to claim 2 wherein said delivery means further comprises a spacer separated from said hand-held inhaler and interposed between said handheld inhaler and said user, said spacer having a first end communicating with said hand-held inhaler through a conduit, and having a second end adapted for delivering a desired dose of inhaled medication into a user's mouth.

21. An apparatus according to claim 2 wherein said microprocessor further comprises output means communicating electronically along a communication path with a remotely located digital computer for transmitting signals representative of said stored data for remote compliance monitoring; and said microprocessor further comprising input means for receiving input signals from said remotely located digital computer for reprogramming said microprocessor means to vary the desired dose of medication inhaled by the patient.

22. An apparatus according to claim 2 further comprising at least one of auditory, visual and vibratory alarm means for notifying a user when to take said medication.

23. An apparatus according to claim 2 wherein said means for performing logical operations or interpretive calculations upon data comprise means for processing selected spirometric measured values such as peak flow to provide feedback of a user's therapeutic response.

24. An apparatus according to claim 2 further comprising sensor means responsive to a user's shaking of the inhaler for turning on said delivery means for subsequent activation by a user.

25. A portable hand-held inhaler device comprising:
a housing adapted to be hand-held by a user;
a canister of inhaled medication received within the housing;
delivery means incorporated in said housing for delivering a desired unit dose of said inhaled medication from said canister;
electronic sensor means incorporated in said housing for measurement of air flow through said delivery means;
microprocessor means incorporated in said housing, comprising means for storage of data, including relative time of activation of said delivery means, and for storing data representative of measured duration and pattern of inspiration through said delivery means for each activation event;
said microprocessor means further comprising means for performing logical operations or interpretive calculations upon said data;
signaling means incorporated in said housing responsive to said microprocessor means for providing feedback to said user, said feedback expressing to the user whether the delivery of medication has been done correctly; and
wherein said signalling means further comprises means for interrogating a patient concerning factors relating to patient status such as symptoms or exposures.

26. A portable hand-held inhaler device comprising:
a housing adapted to be hand-held by a user;
a canister of inhaled medication received within the housing;
delivery means incorporated in said housing for delivering a desired unit dose of said inhaled medication from said canister;
electronic sensor means incorporated in said housing for measurement of air flow through said delivery means;
microprocessor means incorporated in said housing, comprising means for storage of data, including relative time of activation of said delivery means, and for storing data representative of measured duration and pattern of inspiration through said delivery means for each activation event;
said microprocessor means further comprising means for performing logical operations or interpretive calculations upon said data;
signaling means incorporated in said housing, responsive to said microprocessor means for providing feedback to said user, said feedback expressing to the user whether the delivery of medication has been done correctly;
wherein said microprocessor further comprises wireless transmission means for transmitting output signals representative of said stored data to a remotely located computer means for compliance monitoring.

27. A portable hand-held inhaler device comprising:
a housing adapted to be hand-held by a user;
a canister of inhaled medication received within the housing;
delivery means incorporated in said housing for delivering a desired unit dose of said inhaled medication from said canister;
electronic sensor means incorporated in said housing for measurement of air flow through said delivery means;
microprocessor means incorporated in said housing, comprising means for storage of data, including relative time of activation of said delivery means, and for storing data representative of measured duration and pattern of inspiration through said delivery means for each activation event;
said microprocessor means further comprising means for performing logical operations or interpretive calculations upon said data;
signaling means incorporated in said housing, responsive to said microprocessor means for providing feedback to said user, said feedback expressing to the user whether the delivery of medication has been done correctly;
wireless transmission means comprising input means responsive to remotely generated signals for reprogramming said microprocessor to vary the time interval for delivering a desired unit dose of said medication; and
wherein said signalling means is responsive to said remotely generated input signals for indicating a time prescribed for delivery of said dosage of medicine, said means for indicating comprising at least one of the following: indicator lights, auditory tones and vibration.

28. A portable hand-held inhaler device comprising:
a housing adapted to be hand-held by a user;
a container of inhaled medication received within the housing;
delivery means incorporated in said housing for delivering a desired unit dose of said inhaled medication from said container;
electronic sensor means incorporated in said housing for measurement of air flow through said delivery means;
microprocessor means incorporated in said housing, comprising means for storage of data, including relative time of activation of said delivery means, and for storing data representative of measured duration and pattern of inspiration through said delivery means for each activation event;
said microprocessor means further comprising means for performing logical operations or interpretive calculations upon said data;
signaling means incorporated in said housing responsive to said microprocessor means for providing feedback to said user, said feedback expressing to the user whether the delivery of medication has been done correctly;
reprogramming means responsive to said measurement from said electronic sensor means for reprogramming the signalling means to vary the timing of frequency of delivery of medication.

29. A method for administering an air borne medication by a digital computer communicating with a microprocessor incorporated in a portable hand-held inhaler, comprising the steps of:

measuring the values of at least the time, date and inspiration pattern for each use of said inhaler by a patient;

storing said measured values in a microprocessor means incorporated in said portable inhaler;

displaying said measured values in a display unit incorporated in said inhaler for providing interactive feedback with the patient;

retrieving said measured values by wireless communication into a remotely located computer for providing remote compliance monitoring;

visually displaying said measured values on a display unit of said remotely located computer to permit evaluation of a therapeutic effect of said medication upon the patient.

30. A method for administering an air borne medication through a digital computer communicating with a microprocessor incorporated in a portable and hand-held inhaler, comprising the steps of:

measuring the values of at least the time, date and inspiration pattern for each use of said inhaler by a patient;

storing said measured values in a microprocessor means incorporated in said portable inhaler;

displaying said measured values in a display unit incorporated in said inhaler for providing interactive feedback with the patient;

retrieving said measured values along a communication path into a remotely located computer for providing remote compliance monitoring;

visually displaying said measured values on a display unit of said remotely located computer to permit evaluation of a therapeutic effect of said medication upon the patient;

interrogating a patient through the display unit in the inhaler concerning factors affecting inhalation such as exposure to allergens, breathing irritants or the like;

receiving a yes or no answer from the patient in response to the step of interrogating through a switch on the inhaler; and recording the patient's answer as data to be stored in the microprocessor.

31. The method of claim 30 wherein the step of visually displaying said measured values includes the step of further processing of selected spirometric measured values in said remotely located computer means to provide feedback of a patient's therapeutic response.

32. The method of claim 31 wherein said step of further processing comprises the step of displaying a target inspiration pattern on said display unit as a function of time.

33. The method of claim 32 wherein said step of further processing comprises the step of displaying a comparison of a patient's actual inhalation pattern with a prescribed target pattern.

* * * * *

UNITED STATES PATENT AND TRADEMARK OFFICE
CERTIFICATE OF CORRECTION

PATENT NO. : 5,363,842
DATED : November 15, 1994
INVENTOR(S) : David J. Mishelevich, et. al.

It is certified that error appears in the above-indentified patent and that said Letters Patent is hereby corrected as shown below:

Column 13, claim 2, line 18, delete "patent" and insert --patient--.
Column 13, claim 2, line 1, delete "39" and insert --38--.
Column 17, claim 29, line 1, delete "air" and insert --airborne--;
       claim 30, line 1, delete "air" and insert --airborne--;
              line 2, delete "borne".

Signed and Sealed this

Twenty-fourth Day of January, 1995

Attest:

BRUCE LEHMAN

*Attesting Officer*    *Commissioner of Patents and Trademarks*